United States Patent [19]
Tedder

[11] Patent Number: 5,863,720
[45] Date of Patent: Jan. 26, 1999

[54] ONE-POT ASSAY

[75] Inventor: Richard Seton Tedder, London, United Kingdom

[73] Assignee: University College London, London, United Kingdom

[21] Appl. No.: 501,103

[22] PCT Filed: Feb. 15, 1994

[86] PCT No.: PCT/GB94/00298

§ 371 Date: Oct. 27, 1995

§ 102(e) Date: Oct. 27, 1995

[87] PCT Pub. No.: WO94/18570

PCT Pub. Date: Aug. 18, 1994

[30] Foreign Application Priority Data

Feb. 15, 1993 [GB] United Kingdom ............ 9302983

[51] Int. Cl.$^6$ .......................... C12Q 1/70; G01N 33/53; G01N 33/566; G01N 33/569
[52] U.S. Cl. .............................. 435/5; 435/7.1; 435/7.2; 435/973; 436/501
[58] Field of Search .................. 435/5, 7.1, 7.2, 435/973; 436/501

[56] References Cited

U.S. PATENT DOCUMENTS 5,158,869  10/1992  Pouletty et al. .................... 435/7.9

FOREIGN PATENT DOCUMENTS 0238353  9/1987  European Pat. Off. .

OTHER PUBLICATIONS

*Journal of Medical Virology*, vol. 6, 1980, New York, NY USA, pp. 323–332. R.S. Tedder et al. 'Contrasting patterns and frequency of antibodies to the surface, core and e antigens of hepatitis B virus in blood donors and in homosexual patients' see the whole document.

*Journal of Virological Methods*, vol. 11, 1985, Amsterdam NL, pp. 231–239. R.B. Ferns et al. 'Detection of both hepatitis B e antigen and antibody in a single assay using monoclonal reagnets' see the whole document.

Ratnam, S. and A.M. Tobin, "Comparative evaluation of commercial enzyme immunoassay kits for detection of hepatitis B seromarkers", *J. Clin. Microbiol.*, 25:432–434, Feb. 1987.

Ekins and Chu, "Multianalyte microspot immunoassay—microanalytical 'compact disk' of the future", Clin. Chem. 37/11, 1955–1967, 1991.

*Primary Examiner*—Marian C. Knode
*Assistant Examiner*—Brenda G. Brunback
*Attorney, Agent, or Firm*—Iver P. Cooper

[57] ABSTRACT

By conducting two assays for related serological disease markers in a single vessel and arranging for one assay to give a signal which increases with increasing concentration of a first marker while the second assay gives a signal which decreases with increasing concentration of a second marker, and by balancing the respective sizes of the two signals, a combined signal can be generated which indicates the status of an individual or a blood donation with respect to the stage of recovery from the disease.

22 Claims, 3 Drawing Sheets

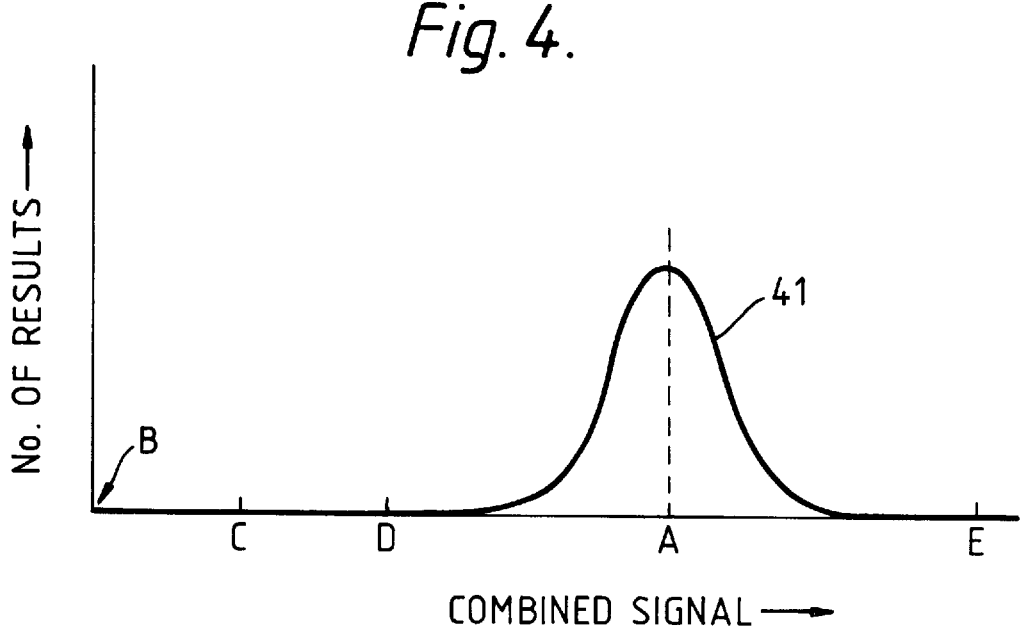

ONE-POT ASSAY

This application is the National Stage of International Application No. PCT/GB94/00298, filed Feb. 15, 1994, under 35 U.S.C. 371.

The present invention relates to a one-pot double serological assay for assessing the status of individuals potentially infected with diseases such as hepatitis B.

Hepatitis B is caused by the hepatitis B virus (HBV) and may be transmitted by blood transfusion (among other means). Screening of donated blood to detect every donation capable of transmitting HBV is highly desirable but presently very complex because a number of different tests need to be completed in order fully to characterise the infection status of the donor and thus to exclude those donations which may transmit the disease. It is now routine to screen donations for the surface antigen of HBV (designated HBsAg) and to discard all those giving a positive result (i.e. those from individuals with an established infection). This is, however, not sufficient to remove all potentially infective donations.

The donors whose samples pass the preliminary screening for HBsAg be divided into a number of categories as follows:

1. Never infected
2. Early (acute) infection.
3. Recently resolved acute infection.
4. Recently resolved chronic infection.
5. Fully recovered from infection and immune.

Of these, only donors from categories 1 and 5 may safely give blood. Donors in category 1 are distinguished by the absence of all HBV markers. Donors in category 2 have no serologically detectable markers but may be identified by the presence of genomic material from HBV using the polymerase chain reaction and hybridisation techniques. Donors in categories 3, 4 and 5 all show some serological markers of HBV infection but currently can be distinguished only on the basis of a complex sequence of tests.

In more detail, individuals in category 3 have cleared the HBsAg itself and mounted an immune response to the core antigen (HBcAg) but have not produced a protective antibody response to the surface antigen. They are therefore serologically identifiable by the presence of antibody against HBcAg (i.e anti-HBc) but low or absent anti-HBs. Individuals in category 4 have had a chronic infection and at some time would have been regarded as "carriers" of HBsAg; they lack anti-HBs but have high levels of anti-HBc. Individuals in category 5, having cleared the infection completely, have both anti-HBc and anti-HBs, some (hereafter category 5a) having very high levels of anti-HBs. Individuals in category 5a represent an important source of material for the production of hyperimmune globulin ("HBIg") which is valuable for passive immunisation against HBV infections. Identification of this subset of immune individuals is therefore important but at present requires further testing.

If these categories were to be distinguished on the basis of conventional single assays, a protocol such as the following would be required:

| a) | Test for HBsAg; | this is mandatory in many blood transfusion programmes, positive donations are discarded. |
|---|---|---|
| b) | Test for anti-HBc; | all positive donations are quarantined. |
| c) | Test positives from test (b) for anti-HBs in a sensitive and quantitative test; | all positives with serum anti-HBs of over 0.1 I.U./ml are reinstated as donors (category 5), all others are discarded (i.e. categories 3 and 4). |
| d) | Test positives from test (c) for anti-HBs in an insensitive mode; | all those found with anti-HBs over 5 I.U./ml are candidates for use in the production of HBIg (i.e. category 5a). |

One objective of the present invention is to provide a "one-pot" assay which will enable donations from individuals in categories 3 and 4 to be excluded from use in blood transfusion and, preferably, also permits identification of individuals in category 5a with high levels of anti-HBs as opposed to those with moderate but safe levels of anti-HBs (hereafter category 5b).

In developing an assay to meet these objectives the present inventors have elucidated certain principles which may be applied to assays of other diseases where certain patterns of antibody or other markers might indicate infectivity or a serious illness.

The present invention therefore provides a one-pot double assay process which process comprises i) contacting, in a single test vessel, first and second capture agents respectively for first and second serological disease markers, with a sample suspected to contain the first and second disease markers, so as to permit any first and second disease markers in the sample to bind to the capture agents;

ii) contacting the capture agents with first and second labelled revealing agents such that the first revealing agent gives a first signal corresponding to the amount of first disease marker in the sample and the second revealing agent gives a second signal corresponding to the amount of second disease marker in the sample; and iii) detecting the combined first and second signals, wherein the strength of the first signal increases monotonically with increasing concentration of first disease marker in the sample and the strength of the second signal decreases monotonically with increasing concentration of second disease marker in the sample.

The invention will be described below with particular reference to assays relating to HBV. The principles elucidated below may equally be applied to other diseases.

The assays relating to HBV are illustrated by the figures of the accompanying drawings in which:

FIG. 1 shows the serum concentration of HBV markers against time since initial infection.

FIG. 2 charts HBV infections in terms of serum anti-HBs versus serum anti-HBc.

FIG. 4 shows the distribution of results for normal serum in a one-pot double assay of the invention.

Figure 1:
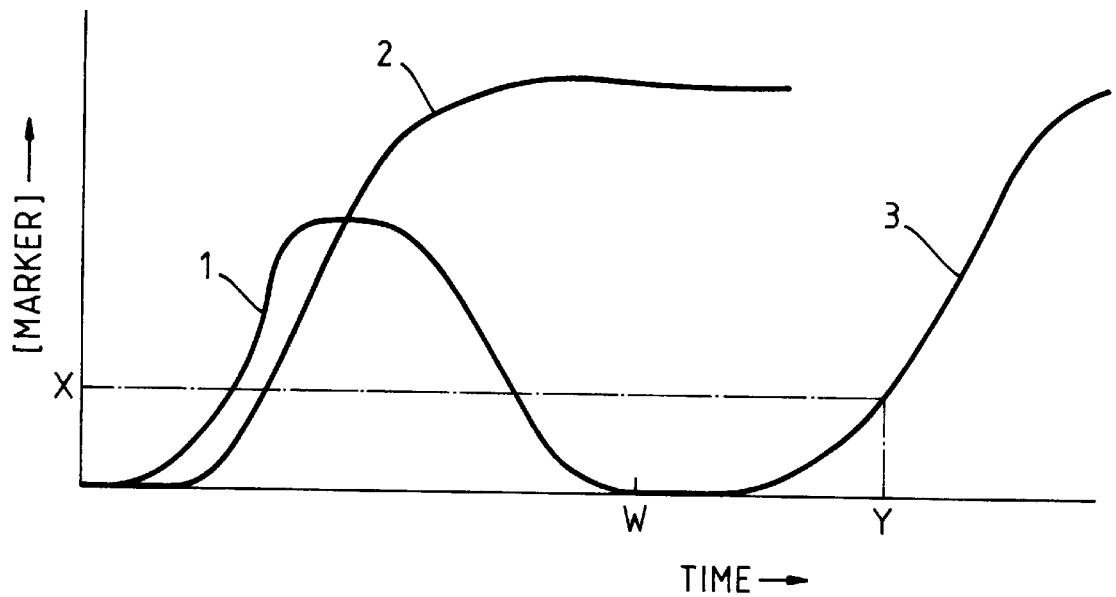
Figure 2:
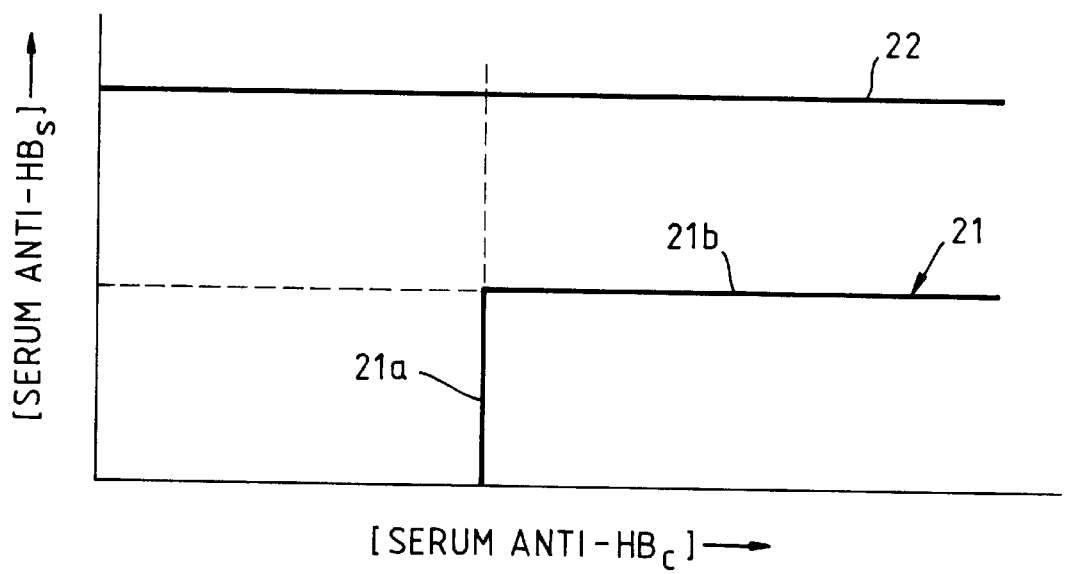

The development of serum antigens and antibodies in HBV infection can be represented by the time course of the infection set out in FIG. 1 and expressed as a plot of serum anti-HBs versus serum anti-HBc as shown in FIG. 2. In FIG. 1, curve 1 represents the concentration of HBsAg throughout the course of HBV infection, falling to zero at time W. The period prior to (left of) time W corresponds with an acute or chronic infection with HBsAg detectable in the serum. Curve 2 represents the concentration of anti-HBc in the serum of an infected individual. Curve 3 represents the concentration of anti-HBs in the serum of an infected individual. The concentrations of anti-HBc and anti-HBs are plotted on arbitrary scales and are not necessarily in proportion.

Concentration X of anti-HBs corresponds with the minimum safe level (100 milli I.U. per ml) corresponding with time Y. In the period between times W and Y an individual is regarded as falling into category 3 or 4. From time Y onwards patients are regarded as recovered and can safely donate blood (category 5).

In FIG. 2, curve 21 represents the boundary between safe and infective donors (categories 3 and 4 below and to the right of the curve, categories 1 and 5 to the left of and above the curve). Curve segment 21a corresponds with the minimum detectable level of serum anti-HBc such that donors to the right of the segment, having detectable serum anti-HBc, are suspect. Curve segment 21b corresponds with the minimum safe level of serum anti-HBs such that donors having levels above the segment have protective antibodies in sufficient amounts and are no longer infective even when serum anti-HBc is detectable. Curve 22 shows the minimum practicable serum concentration of anti-HBs, which may be used for production of HBIg, (i.e. category 5a is above curve 22, category 5b is between curves 21 and 22).

In relation to HBV, the process of the invention comprises carrying out, simultaneously in the same test vessel, an assay for anti-HBs which gives a first signal and an assay for anti-HBc which gives a second signal, wherein the first and second signals are combined such that the combined signal will fall into one of three ranges defined by curves 21 and 22 in FIG. 2, the signals being balanced such that the results for normal serum overlie the category 5b results. In one embodiment, this is achieved by arranging the tests such that first and second signals are acquired by the same detector for instance the first signal increases with increasing concentration of serum anti-HBs and the second signal decreases with increasing concentration of serum anti-HBc, the two signals thus being combined in the detector.

In an alternative embodiment, the signals are acquired by the same detector but the signal from the anti-HBs assay decreases with increasing serum anti-HBs and the signal from the anti-HBc test then increases with increasing serum anti-HBc. In another alternative version the first and second signals are again in opposite phases but are different (eg colour intensities) which may be added or subtracted to give a third colour (or absence of colour) in the category 5b range.

It will be appreciated that it is preferable to modulate the sensitivity of the first and second assays and to arrange that the maximum size of one of the signals is greater than the maximum size of the other.

Figure 3A:
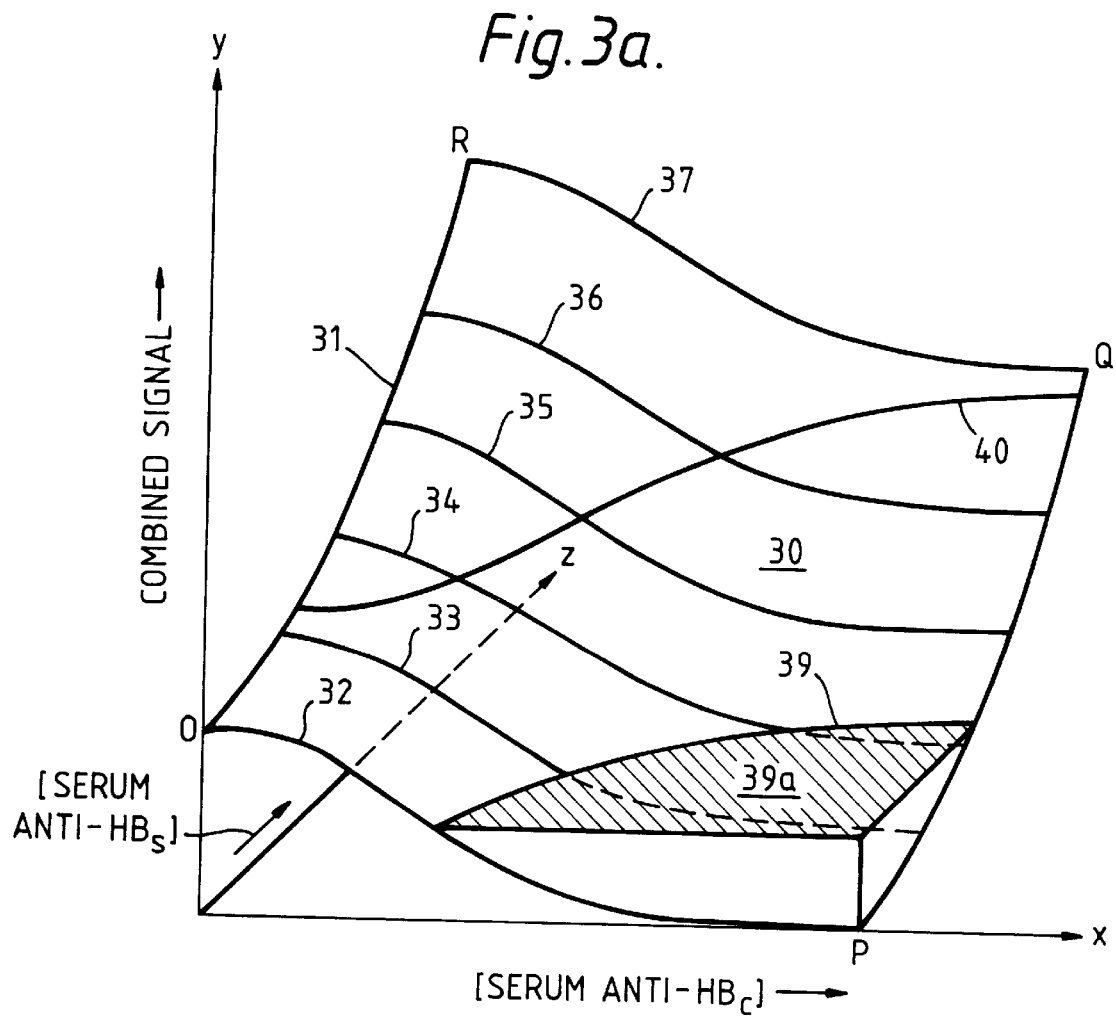
FIG. 3 shows the combined signal values for a one-pot double assay of the invention plotted in 3-dimensions against serum anti-HBs and serum anti-HBc.

This system is illustrated in relation to the first embodiment above in FIG. 3 as follows:

FIG. 3a shows a 3-dimensional plot of combined signal strength (eg cpm of $^{125}$I) on the vertical (y) axis against serum concentrations of anti-HBc (x axis) and anti-HBs (z axis). In this illustration, the first signal increases with increasing serum anti-HBs (cf curve 31) whereas the second signal decreases with increasing serum anti-HBc (cf curve 32). Thus at point O (corresponding with no anti-HBs and no anti-HBc) the combined signal consists only of the maximum value of the second signal. At point P, corresponding with high anti-HBc but no anti-HBs, the combined signal is zero. At point Q, corresponding with high anti-HBs and high anti-HBc the combined signal represents the minimum value of the second signal (i.e. zero) plus the maximum value of the first signal (which is greater than the maximum value of the first signal). At point R, the combined signal represents the sum of the maxima of the first and second signals, corresponding with maximum detectable levels of anti-HBs and absence of anti-HBc. The possible values of the combined signal thus fall on a surface 30, the shape of which is indicated by curves 32 to 37 corresponding to increasing anti-HBs antibody titres up to a maximum at curve 37.

In FIG. 3a the variation of signal strength with anti-HBs and anti-HBc concentrations is shown as being non-linear (this being the usual case) and the surface for all combined signal values is therefore non-planar. It is not essential that the variations are non-linear, nor that the surface is non-planar, however it is important that the two signals are monotonic and that the surface is also unimodal, otherwise it would not be possible to assign cut-off values as described below.

Figure 3B:
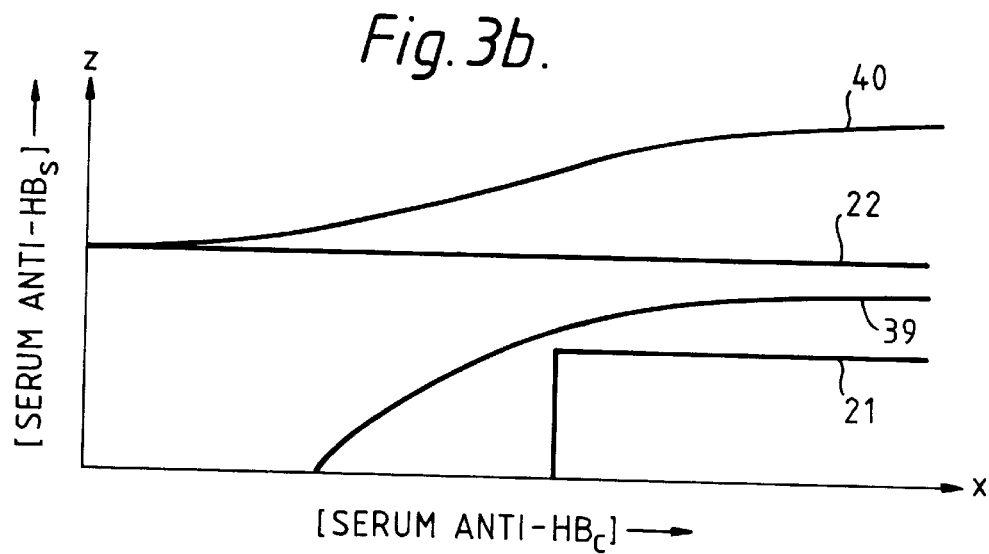

Curve 39 in FIG. 3a represents a preselected cut-off value of the combined signal i.e. it is a contour representing constant combined signal strength as further emphasised by the hatched plane 39a. FIG. 3b is a plot of serum anti-HBs versus serum anti-HBc corresponding with the x-z plane of FIG. 3a; curve 39 from FIG. 3a is shown projected onto the x-z plane. Also shown in FIG. 3b is curve 21 from FIG. 2. Signals less than the cut-off value, hence falling below curve 39 in FIG. 3b are deemed to represent samples not suitable for transfusion. A comparison of curves 39 and 21 in FIG. 3b shows that the cut-off value is selected to allow a safety margin and clearly to encompass all samples having detectable levels of anti-HBc without at least the minimum safe level of anti-HBs. Judicious adjustment of the sensitivity and relative signal strengths of the two assays will minimise the area between curves 21 and 39 thus reducing the number of samples which are discarded despite actually being satisfactory for transfusion.

Returning to FIG. 3a, curve 40 shows another cut-off value of the combined signal. This is preselected to identify category 5a samples. Curve 40 is also shown in FIG. 3b projected onto the x-z plane where it can be seen to fall above curve 22.

In general, assay techniques which afford an increasing signal with increasing serum antibody concentration include those wherein the serum antibody is captured using antigen immobilised as a solid phase and the bound antibody is detected using labelled antigen. Assay techniques which afford a decreasing signal with increasing serum antibody concentration include those wherein the antibody is captured using an excess of antigen immobilised as a solid phase and the residual amount of solid phase antigen is detected using further, labelled antibody. Other assay techniques, for instance sandwich assays and competitive assays, are readily available to those skilled in the art. In the case of HBV at least, many suitable assay techniques for serological markers of infection are already published. For other diseases such as CMV and EBV, suitable assay techniques are also available or may be developed without undue difficulty by those skilled in the art. In relation to assays for HBV markers, reference is made to Tedder et al., J. Med. Virol., 6, 323–332 (1980) and Ferns and Tedder, J. Virol. Methods, 11, 231–239 (1985). The techniques described in these references may readily be adapted for use in anti-HBc and anti-HBs assays for use in the present invention. The choice of the type of assays adopted is not critical to the invention, but it is important that the two signals are in opposite phases (as described above) and it is preferred that the sensitivity and relative signal strengths of the two assays are selected to afford a suitable combined signal.

Labelling and the detection of labels is within the ability of those skilled in the art and many labels and detection techniques are readily available. Examples of suitable labels include radioisotopes, fluorophores, chromophores and enzyme and luminescent labels. It is preferred that the same label is used in both the first and second assays as this facilitates combination of the first and second signals. Thus, for instance, if both assays are conducted using identical radioisotope labels, it is a simple matter to read the combined radioactivity of the two labels, i.e. to obtain the combined signal. Similarly, if identical fluorescent labels are used, the total fluorescent light emission can be detected as the combined signal. This is particularly convenient where the assay is to be automated. In some situations it may be preferable to give a colour signal. In this instance the signal might be the same for both assays so that it is the intensity of colour which provides the combined signal. Alternatively two different colour labels may be used, in which case one assay will give one colour signal and the other a second colour, the combined signal will be a third colour or absence of colour representing the result of colour addition or subtraction (depending on whether a reflection or transmission system is used for reading the colours).

Modulation of sensitivity and signal strengths of such assays is also within the ability of those skilled in the art. Typically this will involve conducting chequerboard tests where one variable is modified against another to define a matrix of results, from which suitable values of each variable may be selected. These techniques will be further explained below by reference to a radioimmunoassay system in accordance with the invention for assessing the potential infectivity of blood donors previously infected with HBV.

A radioimmunoassay in accordance with the present invention comprises a first assay for anti-HBs and a second assay for anti-HBc both conducted in a test vessel comprising a solid substrate having HBcAg and HBsAg (i.e. capture agents) bound to it. The sample and labelled reagents, i.e. radiolabelled anti-HBc and radiolabelled HBsAg (eg $^{125}$I labelled) are added to the substrate simultaneously and incubated therewith or the sample is added and incubated with the substrate and the labelled reagents are added subsequently (together or in any order) and incubated with the substrate. Washing steps may be included as necessary or desirable.

The antibodies bind to the immobilised antigens and labelled anti-HBc binds to the excess immobilised HBcAg. Thus (after washing) the signal from the labelled anti-HBc indicates the amount of remaining immobilised HBcAg and thus decreases with increasing serum anti-HBc. Meanwhile the labelled HBsAg binds to bound anti-HBs and the signal (after washing) due to this label thus increases with increasing serum anti-HBs.

The combined signal from both radiolabels (i.e. measured radioactivity bound to the substrate) is then compared with standards generated using control materials and assigned to one of the areas of FIG. 2.

It is preferred that the assay for anti-HBc is designed to be relatively sensitive and to give a zero signal at high levels of serum anti-HBc and a maximum signal at zero concentration of serum anti-HBc. Between these limits a cut-off signal value is selected corresponding to the minimum detectable level of anti-HBc, samples giving a signal less than the cut-off value would be considered to contain anti-HBc and thus to be unsafe for transfusion in the absence of anti-HBs. In assays of this type a cut-off point of 50% of the maximum signal is generally considered acceptable in a single assay system but in the present one-pot double assay it is preferred to set the cut-off point below 50%, preferably in the region of 25% of the maximum signal, i.e. further distancing the cut-off point from the spread of "normal" results which would be expected from assaying serum containing no anti-HBc. Adjustment of the amount of HBcAg immobilised on the substrate relative to the sample volume and dilution and adjustment of the quantity of labelled anti-HBc relative to the amount of immobilised HBcAg permit the required cut-off point to be set at the preselected fraction (eg 25%) of the maximum signal strength.

The assay for anti-HBs is preferably designed to be less sensitive (than the assay for anti-HBc) but to give a wide spread of signal strengths over the range of anti-HBs concentrations likely to be encountered. It is presently considered that the minimum safe level of anti-HBs is in the region of 100 milli I.U. per ml. and the amounts of immobilised HBsAg relative to the sample volume and dilution, and the amount of labelled HBsAg used relative to the amount of immobilised HBsAg are adjusted such that the combined signal from serum anti-HBs at the minimum safe level added to the signal derived from serum anti-HBc at the minimum detectable level is not more than a second preselected cut-off value, which is clearly below the spread of signals which is generated by normal serum (having effectively zero serum anti-HBc) and is therefore preferably set at about half (50%) of the signal given by normal or "negative" serum (i.e. serum containing no anti-HBc and no anti-HBs).

The second cut-off value represents the combined signal from serum containing the minimum detectable level of anti-HBc and the minimum safe level of anti-HBs. Any category 3 or 4 serum will fall below the second cut-off value as a result of the opposite phases of the two assays as can be seen from FIG. 4.

In FIG. 4, curve 41 represents the normal distribution of signals for normal (category 1) serum in the one-pot double assay and the mid-line of the Gaussian curve at point A thus corresponds with the combined signal generated in the one-pot double assay of the invention for negative serum containing no anti-HBs and no anti-HBc. To the left of point A, i.e. representing decreased combined signal strength, point B represents the minimum signal obtained in the one-pot double assay for samples with high serum anti-HBc and zero serum anti-HBs. Point C represents 25% of the signal strength at A (i.e. 75% inhibition of the maximum signal from the anti-HBc assay) and is the first cut-off value corresponding with serum containing the minimum detectable level of anti-HBc. Point D represents 50% of the signal strength at A and corresponds with the second cut-off value, i.e. the combined signal due to the minimum detectable level of anti-HBc plus the minimum safe level of anti-HBs.

Curve 39 in FIG. 3 corresponds with point D in FIG. 4. Samples having equal to or more than the minimum detectable level of anti-HBc coupled with no more than the minimum safe level of anti-HBs will give a combined signal which is no more than that indicated by point D. In other words, any combination of serum anti-HBs and serum anti-HBc corresponding to categories 3 and 4 gives a combined signal strength at or below (to the left of) the second cut-off value at point D. In order to give a signal to the right of point D the samples must have less than the minimum detectable level of anti-HBc (category 1) or else they contain at least the minimum safe level of anti-HBs whether or not anti-HBc is also present and therefore correspond with category 5.

Although not essential to the invention it is of great benefit to define a further cut-off value (shown in FIG. 4 at E) to the right of A and corresponding to a signal from samples with or without anti-HBc which contain at least the lowest concentration of anti-HBs considered sufficient for the donation to be used for recovery of HBIg, currently considered to be 10 I.U. per ml. Thus any sample having a combined signal at or to the right of point E in FIG. 4 corresponds to Category 5a. Point E in FIG. 4 corresponds with curve 40 in FIG. 3.

Assays according to the present invention are conducted in a single vessel, eg in a single well of a microtitre plate or in a test tube. The capture agents may be in the liquid phase if no washing steps are contemplated or if the test protocol calls for immobilisation or agglutination at a later stage before washing. Otherwise the capture agents will be immobilised ab initio, for instance by binding to the walls of the test vessel or to a solid substrate such as beads in the test vessel. Samples of blood for testing may be pretreated in any conventional manner, eg by removal of erythrocytes (which is particularly important where they would interfere with a colour signal). The signals from the assay of the invention may be detected and recorded in any conventional manner.

The present invention also relates to a kit comprising a test vessel, capture agents and labelled reagents for conducting an assay according to the invention. The kit may optionally also comprises additional materials such as test buffers, washing buffers, revealing agents for detecting the labels, standard solutions of HBsAg, HBcAg, anti-HBs, anti-HBc and negative sera, or lyophilised powders for reconstitution and optionally also comprises instructions for conducting the one-pot assay.

The invention will now be illustrated by the following Examples which are not intended to limit the scope of protection in any way.

EXAMPLE 1

Radioimmunoassay Assays were conducted in microtitre plate wells coated with HBsAg and HBcAg as capture agents. Test sera (100 µl each) were incubated in the wells at 45° C. for two hours. Revealing agents, respectively $^{125}$I-labelled HBsAg and $^{125}$I-labelled anti-HBc, were added (100 µl total) and incubated as before. After a final wash, label-binding was determined by counting in a multi-well counter.

The effects of various concentrations of anti-HBc alone and of various concentrations of anti-HBs in the presence of low level anti-HBc were investigated.

The test sera and results are set out below:

| Test Material | $^{125}$I binding (dpm) |
|---|---|
| Normal human serum (NHS)* | 2,500 |
| NHS plus 1 anti-HBc (cut off)** | 1,179 |
| NHS plus 1/100 anti-HBc | 738 |
| NHS plus 1/30 anti-HBc | 593 |
| NHS plus undiluted anti-HBc+ | 199 |
| Weak anti-HBc plus 1/100 anti-HBs++ | 744 |
| Weak anti-HBc plus 1/30 anti-HBs | 1,015 |
| Weak anti-HBc plus 1/10 anti-HBs | 1,682 |

*NHS is pooled standard material which has tested negative for all known HBV markers.
**this is a dilution of anti-HBc selected to conform with the cut-off point in commercially available diagnostic kits.
+undiluted anti-HBc is standard material representing the amount of anti-HBc found in the serum of a majority of previously infected patients [Tedder, R. S. et al., J.Med.Virol., 6, 323–332 (1980)]
++undiluted anti-HBs is standard material obtained by pooling serum from vaccinated individuals [ibid].

This assay shows that the addition of low levels of anti-HBs to a serum can mask detection of low but otherwise detectable levels of anti-HBc (eg 1/30 anti-HBc) in that serum.

EXAMPLE 2

Radioimmunoassay

A second assay was conducted as set out for Example 1. The assay was calibrated using control sera giving results as follows:

| Sample | $^{125}$I (dpm) |
|---|---|
| NHS | 916 |
| Cut off* | 659 |
| Anti-HBs | 4153 |

*i.e 1/30 anti HBc plus 1/100 anti-HBs

This permitted identification of the following limit values ($^{125}$I,dpm)

| Anti-core only | <659 |
|---|---|
| Negative (uninfected) | 659 to 1318 |
| safe | >1318 |

Serum samples submitted for routine diagnostic assays were also tested in the assay of the invention. In the table below the samples are classified according to the results of the routine assays into the following groups:

| "U" (Uninfected) | No detectable markers of HBV infection or immunisation against HBV. |
|---|---|
| "C" (Anti-HBc alone) | These were defined to contain anti-HBc by competitive RIA but were unreactive in assays for anti-HBs and HBsAg. |
| "I" (Immune sera) | These were defined as sera containing both anti-HBc and anti-HBs. |
| "S" (Anti-HBs alone) | These were defined to contain anti-HBs alone (>10 IU/ml) by immunometric RIA but were unreactive in assays for HBSAg and anti-HBc. These were taken from immunised patients. |

The table below also shows the results of the assay according to the invention and the interpretation of that result which can be compared with the results of the routine diagnostic assays.

| Test Sera | Group | Notes* | Result ($^{125}$ dpm) | Interpretation |
|---|---|---|---|---|
| 1. | U | | 971 | Negative |
| 2. | U | | 971 | Negative |
| 3. | U | | 916 | Negative |
| 4. | U | | 911 | Negative |
| 5. | U | | 898 | Negative |
| 6. | U | | 1,004 | Negative |
| 7. | U | | 1,047 | Negative |
| 8. | U | | 987 | Negative |
| 9. | C | Weak anti-HBC (at c/o) | 609 | Weak anti-core |
| 10. | C | | 152 | anti-core |
| 11. | C | weak anti-HBc (above c/o) | 660 | weak anti-core |
| 12. | C | | 239 | anti-core |
| 13. | C | | 299 | anti-core |
| 14. | C | | 225 | anti-core |
| 15. | C | | 584 | anti-core |
| 16. | I | 20 | 154 | anti-core |
| 17. | I | >250 | 1,807 | anti-HBs |

| Test Sera | Group | Notes* | Result ($^{125}$ dpm) | Interpretation |
|---|---|---|---|---|
| 18. | I | 220 | 3,075 | anti-HBs |
| 19. | I | 50 | 279 | anti-core |
| 20. | I | >250 | 1,330 | anti-HBs |
| 21. | I | >250 | 4,249 | anti-HBs |
| 22. | I | >250 | 2,737 | anti-HBs |
| 23. | I | 250 | 1,409 | anti-HBs |
| 24. | S | 100 | 996 | Negative |
| 25. | S | 100 | 1,227 | Negative |
| 26. | S | 50 | 1,384 | anti-HBs |
| 27. | S | ≈15 | 1,018 | Negative |
| 28. | S | 200 | 1,151 | Negative |
| 29. | S | >250 | 2,707 | anti-HBs |
| 30. | S | >250 | 22,174 | anti-HBs |
| 31. | S | 130 | 1,185 | Negative |

*For sera in group I (anti-HBC plus anti-HBs) and in group (anti-HBs only) the concentration of HBs is given in mIU.

All "negative" and "anti-HBs" sera (interpretation column) are safe for blood transfusion.

The assay was able to differentiate between sera containing anti-HBc alone and sera containing anti-HBs at high level, with or without anti-HBc. In addition it correctly assigned sera containing anti-HBc with low but protective levels of anti-HBs to the "anti-core only" range. This is important in that the assay correctly identified sera which contained HBV markers likely to be associated with disease transmission by blood donation; examples of such sera are samples 13, 14, 16 and 19, being those which are anti-HBc positive but which contained anti-HBs <200 mIV.

EXAMPLE 3

Elisa

In this experiment samples were incubated for one hour at 37° C. in test wells coated with HBsAg and HBcAg. Anti-HBs and anti-HBc, each labelled with horseradish peroxidase (HRPO) were added to the well and incubated for one hour. After a second washing, the bound conjugate (comprising both HBsAg-HRPO and anti-HBc-HRPO) was detected by incubating with substrate (TMB). The colour reaction was stopped and the OD of the reaction determined. The results were as substrate follows:

| Test Material | OD 450 nm |
|---|---|
| Normal human sera (NHS) | 1.05 |
| NHS containing 250 mIU anti-HBs | 1.20 |
| NHS containing 500 mIU anti-HBs | 1.77 |
| NHS containing anti-HBc alone | 0.21 |
| NHS containing anti-HBc and 250 mIU anti-HBs | 0.88 |

In this experiment the assay as described was able to detect serum containing only anti-HBc and the signal indicating anti-HBc was quenched by the addition of 250 mIU/ml anti-HBs.

EXAMPLE 4

Elisa

A further experiment was conducted as in Example 3 but with the anti-HBc components altered twofold (reduced conjugate of anti-HBc) in order to increase the sensitivity of the anti-HBc detection. All other parameters remained unchanged. The results were as follows:

| Test Material | OD 450 nm |
|---|---|
| NHS | 0.86 |
| NHS containing 250 mIU anti-HBs | 1.25 |
| NHS containing 500 mIU anti-HBs | 1.52 |
| NHS containing anti-HBc alone | 0.10 |
| NHS containing anti-HBc and 250 mIU anti HBc | 0.73 |

The assay was again able to detect the serum containing anti-HBc alone. There was better discrimination between the normal human serum and serum containing anti-HBs alone as a result of the modification in the anti-HBc components.

I claim:

1. A serological assay process for detecting a hepatitis B infection which comprises
    i) contacting, in a single test vessel, first and second capture agents respectively for first and second serological markers of hepatitis B infection, with a sample derived from a patient suspected to suffer from a hepatitis B infection, said sample suspected to contain said first and second markers, so as to permit any first and second disease markers in said sample to bind to said capture agents;
    ii) then contacting said capture agents with first and second labelled revealing agents bearing first and second labels respectively such that said first revealing agent gives a first signal corresponding to the amount of said first marker in said sample and said second revealing agent gives a second signal combinable with said first signal and corresponding to the amount of said second marker in said sample;
    iii) combining said first and second signals into a third signal,
    iv) detecting said third signal, and
    v) correlating the presence or absence of a heptitis B infection in said patient with the strength of the third signal, wherein the strength of said first signal increases monotonically with increasing concentration of said first marker in said sample and the strength of said second signal decreases monotonically with increasing concentration of said second marker in said sample.

2. A process according to claim 1 weherein said sample is a blood donation.

3. A process according to claim 1 wherein said first marker is antibody against hepatitis B surface antigen.

4. A process according to claim 3 wherein said first capture agent is hepatitis B surface antigen.

5. A process according to claim 3 wherein said first revealing agent is labelled hepatitis B surface antigen.

6. A process according to claim 1 wherein said second marker is antibody against hepatitis B core antigen.

7. A process according to claim 6 wherein said second capture agent is hepatitis B core antigen.

8. A process according to claim 6 wherein said second revealing agent is labelled antibody against hepatitis B core antigen.

9. A process according to claim 1 wherein said first and second capture agents are bound to solid supports.

10. A process according to claim 9 wherein said first and second capture agents are bound to the same solid support.

11. A process according to claim 10 wherein said solid support is the surface of a well of a microtitre plate.

12. A process according claim 1 wherein said first and second revealing agents bear the same label.

13. A process according to claim 12 wherein said label is a radioisotope.

14. A process according to claim 13 wherein said label is $^{125}$I.

15. A process according to claim 12 wherein said label is an enzyme.

16. A process according to claim 15 wherein said label is horseradish peroxidase.

17. A process according to claim 16 wherein said first and second revealing agents bear the same label, and said label is selected from the group consisting of radioisotopes and enzymes.

18. A process according to claim 17 wherein said sample is a blood donation.

19. The process of claim 1 in which the first label is a first color and the second label is of a second and different color, and said first and second colors are combined to yield a third color or an absence of color as the third signal.

20. The process of claim 1 wherein said labels are both fluorescent labels, and the third signal is the total fluorescent light emission.

21. The process of claim 1 wherein said labels are both radioactive labels, and the third signal is the combined radioactivity.

22. A serological assay process for detecting a hepatitis B infection which comprises (i) contacting, in a single test vessel, first and second capture agents respectively for first and second serological markers of hepatitis B infection, with a sample derived from a patient suspected to suffer from a hepatitis B infection, said sample suspected to contain said first and second markers, so as to permit any first and second markers in said sample to bind to said capture agents;

(ii) then contacting said capture agents with first and second labelled revealing agents, bearing first and second labels, respectively, such that said first revealing agent gives a first signal corresponding to the amount of said first marker in said sample and said second revealing agent gives a second signal combinable with said first signal and corresponding to the amount of said second marker in said sample;

iii) combining said first and second signals into a third signal, iv) detecting said third signal, and (v) correlating the presence or absence of a hepatitis B infection in said patients with the strength of the third signals, wherein the strength of said first signal increases monotonically with increasing concentration of said first marker in said sample and the strength of said second signal decreases monotonically with increasing concentration of said second marker in said sample, the first and second disease markers being markers of hepatitis B infection, the first marker being antibody against hepatitis B surface antigen, said first capture agent being hepatitis B surface antigen, said first revealing agent being labelled hepatitis B surface antigen, said second marker being antibody against hepatitis B core antigen, said second capture agent being hepatitis B core antigen, said second revealing agent being labelled antibody against hepatitis B core antigen and said first and second capture agents being bound to the same solid support.

* * * * *